United States Patent
Bobrow et al.

(10) Patent No.: US 6,355,443 B1
(45) Date of Patent: Mar. 12, 2002

(54) 4-(4-HYDROXYSTYRYL) PYRIDINE-CONTAINING SUBSTRATES FOR AN ANALYTE DEPENDENT ENZYME ACTIVATION SYSTEM

(76) Inventors: Mark Norman Bobrow, 11 Battle Green Rd., Lexington, MA (US) 02421; Kevin Aaron Roth, 526 Webster Forest, Webster Groves, MI (US) 63119

( * ) Notice: Subject to any disclaimer, the term of this patent is extended or adjusted under 35 U.S.C. 154(b) by 0 days.

(21) Appl. No.: 09/526,594

(22) Filed: Mar. 16, 2000

Related U.S. Application Data

(60) Provisional application No. 60/124,826, filed on Mar. 17, 1999.

(51) Int. Cl.$^7$ .................. G01N 33/567; G01N 33/533; G01N 33/534; G01N 33/535
(52) U.S. Cl. .................. 435/7.21; 435/7.5; 435/7.72; 435/7.9; 435/7.91; 435/7.92; 435/28; 436/40.52; 436/177; 436/960; 436/544; 436/545; 436/546
(58) Field of Search .................. 435/7.9, 7.91, 435/7.92, 28, 975, 40.52, 177, 960, 7.5, 7.21, 7.72; 436/544, 545, 546

(56) References Cited

U.S. PATENT DOCUMENTS

| | | | |
|---|---|---|---|
| 5,196,306 A | 3/1993 | Bobrow et al. | 435/7.9 |
| 5,583,001 A | 12/1996 | Bobrow et al. | 435/7.5 |
| 5,731,158 A | 3/1998 | Bobrow et al. | 435/7.5 |
| 5,863,748 A | 1/1999 | Bobrow | 435/7.9 |

OTHER PUBLICATIONS

Mishra, B. K. et al. Reversal in Solvatochromism: An Et(30) switch for a new class of cyanine dyes. Bull. Chem. Soc. Jpn. 1996, vol. 69, No. 9, pp. 2581–2584, especially compounds 22–4 on p. 2581.

Dubur, G. Y. et al. Fluorescent probes based on styrylpyridinium derivatives: optical properties and membrane binding. J. Biochem. Biophys. Method. 1984, vol. 10, pp. 123–134, especially compound IIIc on p. 124.

Bobrow et al. (1989) Catalyzed reporter deposition, a novel method of signal amplification. I. Application to immunoassays. Journal of Immunological Methods, 125:279–285.

Bobrow et al. (1991) Catalyzed reporter deposition, a novel method of signal amplification. II. Application to membrane immunoassays. Journal of Immunological Methods, 137:103–112.

Loew et al. (1978) Charge shift optical probes of membrane potential. Theory. Biochemistry, vol. 17, No. 19, pp. 4065–4071.

Loew et al. (1979) Evidence for a charge–shift electrochromic mechanism in a probe of membrane potential. Nature, vol. 281: 497–499.

Loew et al. (1981) Charge–shift probes of membrane potential. A probable electrochromic mechanism for p–Aminostyrylpyridinium probes on a hemispherical lipid bilayer. Biophys. J., vol. 34:353–365..

Loew (1982) Design and characterization of electrochromic membrane probes. Journal of Biochemical and Biophysical Methods, 6:243–260.

*Primary Examiner*—Mary E. Ceperley
(74) *Attorney, Agent, or Firm*—Gifford, Krass, Groh, Sprinkle, Anderson & Citkowski, P.C.

(57) ABSTRACT

4-(4-hydroxystyryl) pyridine-containing compounds are disclosed as substrates for use in assays. Also, a method for detecting or quantitating an analyte is provided which includes reacting an enzyme with a 4-(4-hydroxystyryl) pyridine-containing compound to form a reactive intermediate wherein the reactive intermediate deposits covalently on a surface by binding to a receptor, wherein deposited reactive intermediates either directly or indirectly through a label generate a signal which can be detected or quantitated.

17 Claims, 2 Drawing Sheets

(2 of 2 Drawing Sheet(s) Filed in Color)

4-(4-HYDROXYSTYRYL) PYRIDINE-CONTAINING SUBSTRATES FOR AN ANALYTE DEPENDENT ENZYME ACTIVATION SYSTEM

RELATED APPLICATION

This application claims priority of U.S. Provisional Application Ser. No. 60/124,826 filed Mar. 17, 1999.

FIELD OF THE INVENTION

This invention relates to 4-(4-hydroxystyryl) pyridine-containing compounds and the use of 4-(4-hydroxystyryl) pyridine-containing compounds as peroxidase enzyme substrates in a variety of applications such as catalyzed reporter deposition.

BACKGROUND OF THE INVENTION

Peroxidase, because of its high turnover rate, good stability, and availability is widely used in enzyme-based analytical methods. For example, horseradish peroxidase (HIW) (EC 1.11.1.7) catalyzes the oxidation of a large variety of hydrogen-donating substrates with hydrogen peroxide. HRP is also one of the preferred enzymes for use in catalyzed reporter deposition.

Catalyzed reporter deposition (CARD) is a novel method of signal amplification which constitutes the subject matter of U.S. Pat. Nos. 5,731,158, 5,583,001 and 5,196,306. It is also discussed in Bobrow et al., Journal of Immunological Methods, 125: 279–285 (1989) and in Bobrow et al., Journal of Immunological Methods, 137:103–112 (1991).

The CARD method utilizes an analyte-dependent enzyme activation system ("ADEAS") to catalyze the deposition of reporter or hapten groups (labels) onto the solid phase of an assay platform. These enzymatically deposited labels are detected directly or indirectly, resulting in signal amplification and improved detection limits. In a preferred embodiment, HRP is the enzyme.

HRP reacts with a conjugate consisting of a labeled compound incorporated into a peroxidase substrate. When the enzyme and the compound react, a reactive intermediate is formed which deposits covalently wherever receptor for the activated reactive intermediate is immobilized. Examples of such compounds which have been described include substituted phenols such as biotinyl-tyramide, fluorescein tyramide and p-hydroxycinnamoyl-containing substrates disclosed in U.S. Pat. No. 5,863,748.

For analytical use, peroxidase substrates have been used to generate products which become colored, fluorescent or chemiluminescent. These products either remain soluble or become insoluble and precipitate on the surface. The CARD method differs in that the reactive intermediates become covalently bound to the surface.

Styryl-pyridinium compounds are well known for use as, for example, electrochromic membrane probes, Loew, *Journal of Biochemical and Biophysical Methods*, 6 (1982) 243–260; Loew and Simpson, *Biophys. J*, Vol. 34, June 1981, 353–365; Loew et al., *Biochemistry*, Vol. 17, No. 19, 1978, 4065–4071; and Loew et al., *Nature*, Vol. 281, Oct. 11, 1979, 497–499. The use of styryl-pyridinium compounds as probes of membrane potential is specifically set forth in these publications. However, none of these publications teach the use of styryl-pyridinium compounds as substrates.

Typically, fluorescent compounds are used as labels for CARD and other methods. The greater the intensity of fluorescence and the greater the Stokes shift (large spread between excitation and emission maxima) of a fluorescent compound, the lower the detectable limit of the chosen material.

Accordingly, it would be advantageous and desirable to have a labeled compounds which have a high degree of reactivity, a very large Stokes shift, and which also are highly fluorescent when dry, as substrates for use in enzyme assays such as CARD assays.

SUMMARY OF THE INVENTION

The present invention relates to labeled 4-(4-hydroxystyryl) pyridine-containing compounds incorporated into peroxidase-based substrates and the use of these substrates in assays. The present invention also relates to 4-(4-hydroxystyryl) pyridine-containing compounds having the structure:

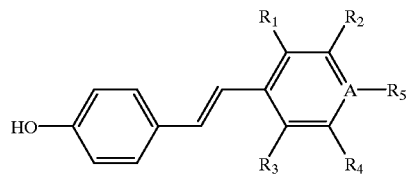

wherein $R_1$, $R_2$, $R_3$, and $R_4$ are independently H or —X—L, $R_5$ is an electron pair or —X—L, X is a linker group capable of linking L to a 4-(4-hydroxystyryl) pyridine moiety, L is a detectable label, A is N or $N^+$, and wherein when $R_1$, $R_2$, $R_3$, and $R_4$ are H, $R_5$ is —X—L and A is $N^+$ and wherein when any of $R_1$–$R_4$ is —X—L, A is N or a member of a specific binding pair. The compound itself is fluorescent and may serve as a label. If L is chosen as an appropriate label, fluorescence amplification may be achieved without the use of CARD.

Also disclosed are 4-(4-hydroxystyryl) pyridine-containing compounds incorporated into peroxidase-based substrates and the use of these substrates in assays. The compounds having the structure:

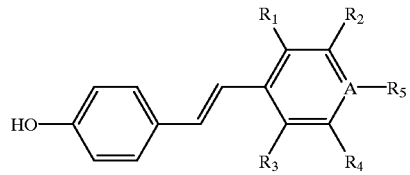

wherein $R_1$, $R_2$, $R_3$, and $R_4$ are H or Z; $R_5$ is an electron pair or Z, Z is a linear, a branched alkyl, a substituted alkyl, heteroalkyl or substituted heteroalkyl wherein the heteroatom is selected from the group consisting of N, O, or S; A is N or $N^+$ and wherein when $R_1$, $R_2$, $R_3$, and $R_4$ are H, $R_5$ is Z and A is $N^+$ and wherein when any of $R_1$–$R_4$ is Z, A is N.

Also disclosed herein is the use of 4-(4-hydroxystyryl) pyridine-containing compounds in assays for detecting or quantitating the presence or absence of an analyte in a sample which may or may not include the use of CARD to amplify the reporter signal.

BRIEF DESCRIPTION OF THE FIGURES

The file of this patent contains at least one drawing executed in color. Copies of this patent with color drawings (s) will be provided by the Patent and Trademark Office upon request and payment of the necessary fee.

Other advantages of the present invention will be readily appreciated as the same becomes better understood by reference to the following detailed description when considered in connection with the accompanying drawings wherein.

DETAILED DESCRIPTION OF THE INVENTION

Figure 1A:
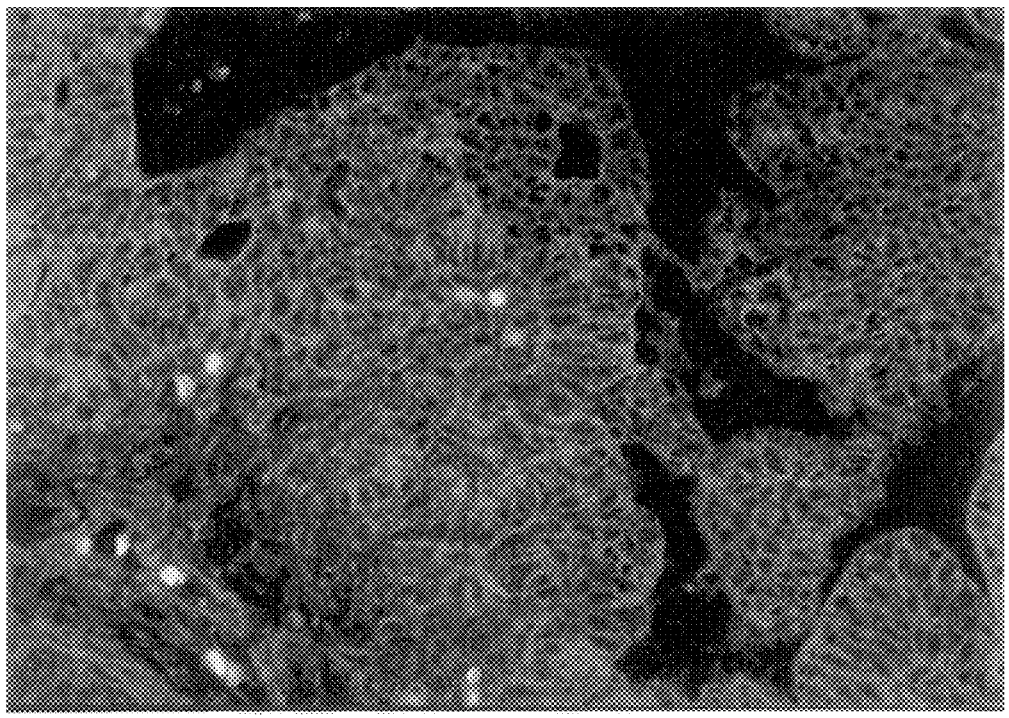
FIG. 1A is a photomicrograph illustrating that sections of mouse intestine incubated in PBS-BB without wheat germ agglutinin had no specific labeling.

As disclosed herein, the present invention relates to the use of 4-(4-hydroxystyryl) pyridine-containing compounds incorporated into peroxidase substrates. The term analyte dependent enzyme activation system (ADEAS) refers to an enzyme system wherein (i) at least one enzyme is coupled, in any manner known to those skilled in the art, to a member of a specific binding pair, or (ii) the enzyme need not be coupled to a member of a specific binding pair when it is the analyte. The enzyme, either by itself or in connection with a second enzyme, catalyzes the formation of a reactive intermediate which then is deposited wherever there is a receptor for the reactive intermediate.

The term surface as used herein means any solid support or phase known to those skilled in the art including cells, tissues, membranes, slides, and beads.

The term amplification as used herein means amplification of reporter signal.

The term reactive intermediate means the 4-(4-hydroxystyryl) pyridine-containing compound has been primed by the enzyme to bind to the receptor.

The term receptor means a site which will bind to the reactive intermediate through the formation of a covalent bond.

The term detectably labeled means that the 4-(4-hydroxystyryl) pyridine-containing compound, in addition to the substrate characteristics imparted by the phenolic moiety, is also fluorescent due to the additional ring member bound through the styryl linkage. The compound may also be detectably labeled by coupling it to a reporter or an unlabeled first member of a specific binding pair. In the case in which the compound is coupled to an unlabeled member of a specific binding pair, after the reactive intermediate is covalently bound to the receptor, the substrate-specific binding pair complex is reacted with the second member of the binding pair which is coupled to a reporter.

Members of specific binding pairs suitable for use in practicing the invention can be of the immune or non-immune type. Immune specific binding pairs are exemplified by antigen/antibody systems or hapten/anti-hapten systems such as dinitrophenyl (DNP)-anti-DNP. The antibody member, whether polyclonal, monoclonal or an immunoreactive fragment thereof, of the binding pair can be produced by customary methods familiar to those skilled in the art. The terms immunoreactive antibody fragment or immunoreactive fragment mean fragments which contain the binding region of the antibody. Such fragments may be Fab type fragments which are defined as fragments devoid of the Fc portion, e.g., Fab, Fab' and F(ab')2 fragments, or may be so-called "half molecule" fragments obtained by reductive cleavage of the disulfide bonds connecting the heavy chain components of the intact antibody. If the antigen member of the specific binding pair is not immunogenic, e.g., a hapten, it can be covalently coupled to a carrier protein to render it immunogenic.

Non-immune binding pairs include systems wherein the two components share a natural affinity for each other but are not antibodies. Exemplary non-immune binding pairs are biotin-avidin or biotin-streptavidin, folic acid-folate binding protein, complementary probe nucleic acids, etc. Also included are non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters, sulfonyl halides, and coupler dyes such as 3-methyl-2-benzothiazolinone hydrazone (MBTH) and 3-(dimethyl-amino) benzoic acid (DMAB), etc.

The term deposition means directed binding of a reactive intermediate to the receptor which results from the formation of a covalent bond.

The enzyme catalyzes the deposition of a 4-(4-hydroxystyryl) pyridine-containing compound by converting the compound to a reactive intermediate which is capable of covalently binding to a receptor.

The instant invention also concerns the 4-(4-hydroxystyryl) pyridine-containing compounds which heretofore have not been described as enzyme substrates.

Enzymes suitable for use with 4-(4-hydroxystyryl) pyridine-containing compounds of the invention include oxidoreductases. More particularly, peroxidases can be employed. One particularly preferred enzyme which is suitable for the novel substrates of the invention is a horseradish peroxidase.

It has been found, surprisingly and unexpectedly, that a peroxidase substrate incorporating a novel 4-(4-hydroxystyryl) pyridine-containing compound significantly improves the sensitivity of catalyzed reporter deposition beyond the level currently achieved using previously described fluorescent conjugates and exhibits a very large Stokes shift.

In another embodiment, the invention relates to 4-(4-hydroxystyryl) pyridine-containing compounds having the structure:

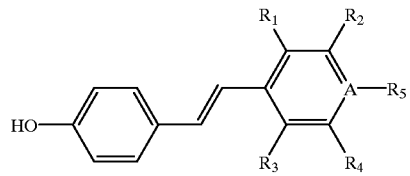

wherein $R_1$, $R_2$, $R_3$, and $R_4$ are independently H or —X—L, $R_5$ is an electron pair or —X—L, X is a linker group capable of linking L to a 4-(4-hydroxystyryl) pyridine moiety, L is a detectable label, A is N or $N^+$, and wherein when $R_1$, $R_2$, $R_3$, and $R_4$ are H, $R_5$ is —X—L and A is $N^+$ and wherein when any of $R_1$–$R_4$ is —X—L, A is N.

In another embodiment, the invention relates to 4-(4-hydroxystyryl) pyridine-containing compounds having the structure:

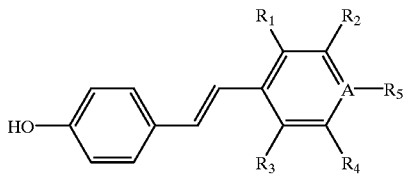

wherein $R_1$, $R_2$, $R_3$, and $R_4$ are H or Z; $R_5$ is an electron pair or Z, Z is a linear alkyl, a branched alkyl, a substituted alkyl, heteroalkyl or substituted heteroalkyl wherein the heteroatom is selected from the group consisting of N, O, or S; A is N or $N^+$ and wherein when $R_1$, $R_2$, $R_3$, and $R_4$ are H, $R_5$ is Z and A is $N^+$ and wherein when any of $R_1$–$R_4$ is Z, A is N.

Examples of suitable 4-(4-hydroxystyryl) pyridine-containing compounds include, for example,

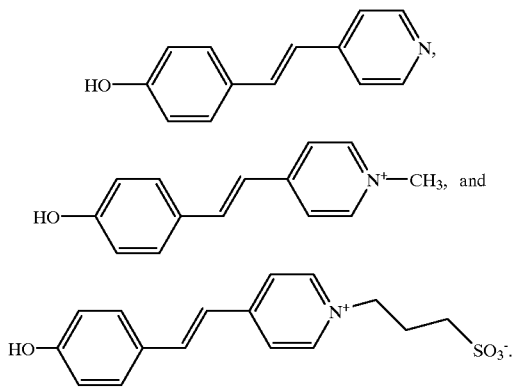

The term "heteroalkyl" means an alkyl group where one or more carbon atom is replaced with a heteroatom.

The term "substituted" means that the organic base radical has one or more substituents. For example, substituted heteroalkyl means a heteroalkyl radical that has one or more substituents. Substituents can include, but are not limited to, —OH, —COOH, —$NH_2$, and —SH. The bonds connecting the heteroalkyl can include single and/or double bonds.

A wide variety of detectable labels are available for linking to the 4-(4-hydroxystyryl) pyridine moiety, and the present invention is not limited to any specific label. The detectable label can be a reporter such as a radioactive isotope such as $^{125}$I, enzymes, fluorogenic reagents such as fluorescein or tetramethylrhodamine, chemiluminescent reagents, or electrochemical materials. The detectable label can also be a member of a specific binding pair as described above. Other labels will be readily apparent to one of skill in the art.

Enzymes which can be used to practice the invention when the reporter is an enzyme include hydrolases, lyases, oxidoreductases, transferases, isomerases and ligases. Some preferred examples are phosphatases, esterases, glycosidases and peroxidases. Specific examples include alkaline phosphatase, lipases, beta-galactosidase and horseradish peroxidase. If an enzyme is used as a reporter, it can be the same as or different from the enzyme or enzymes used in creating the reactive intermediate.

The linker, X, group can be virtually any linker group capable of linking the detectable label to the 4-(4-hydroxystyryl) pyridine moiety, and the invention is not limited to the use of any specific linkers. Any linear or branched alkyl ($C_1$–$C_{10}$ alkyl) or aryl group can serve as a linker, the only requirement being that it links the 4-(4-hydroxystyryl) pyridine moiety with the label. For example, haloalkyl compounds such as bromohexanoic acid will react with the 4-(4-hydroxystyryl) pyridine moiety resulting in the formation of a 4-(4-hydroxystyryl) N-(6-hexanoyl) pyridine compound. The hexanoic acid group can then be used to link amine containing labels. An example of a compound in accordance with the present invention having a linker group attaching a detectable biotin group to a 4-(4-hydroxystyryl) pyridine moiety has the structure

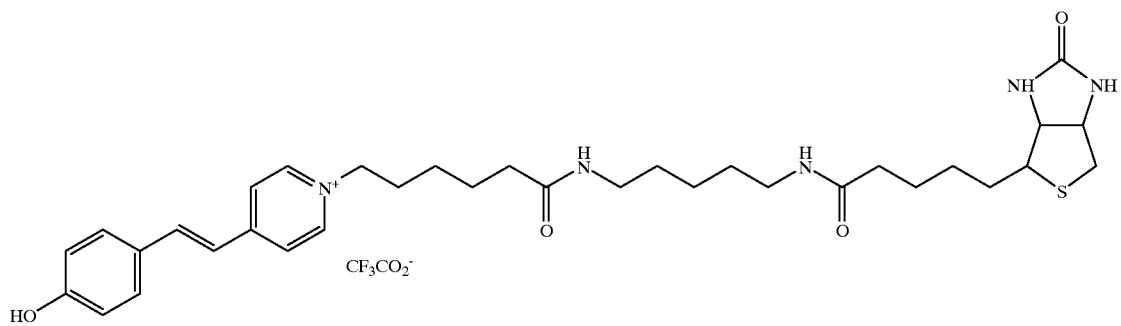

wherein the linker group is —$(CH_2)_5CONH(CH_2)_5NH$—.

When a 4-(4-hydroxystyryl) pyridine-containing compound of the present invention is reacted with an enzyme, the resultant reactive intermediate is capable of binding to a receptor. The reactive intermediate binds to the receptor via a covalent bond. The novelty of the reactive intermediate covalently binding with receptors may be attributable to electron rich moieties of the receptor. An exogenous receptor means a receptor which does not originate within the assay. It can be immobilized on the surface of a support prior to adding the conjugate to the reaction mixture.

In still another embodiment, the invention relates to the use of such 4-(4-hydroxystyryl) pyridine-containing com pounds for detecting or quantitating the presence or absence of an analyte in a sample in which catalyzed reporter deposition is used to amplify the reporter signal.

The compounds of the present invention can be synthesized using conventional coupling and labeling techniques.

As was noted above, many linker groups attached to detectable labels are commercially available. These commercially available linker groups can be reacted with 4-(4-hydroxystyryl) pyridine-containing compounds using conventional protocols well known to those skilled in the art.

The examples presented below are intended to illustrate particular embodiments of the invention and are not intended to limit the scope of the specification, including the claims, in any way.

EXPERIMENTAL DATA

EXAMPLE 1

Sensitive HRP localization using a 4-(4-hydroxystyryl) pyridine containing compound.

Sections of paraffin-embedded mouse intestine were deparaffinized and non-specific binding sites blocked by treatment for thirty minutes in PBS-blocking buffer (PBS-BB; 0.1M phosphate buffered saline, pH 7.2; 1.0% bovine serum albumin, 0.2% non-fat powdered milk, and 0.3% Triton X-100). Horseradish peroxidase (HRP) conjugated wheat germ agglutinin (Sigma; St. Louis, Mo.) at a concentration of 0.5 µg/ml in PBS-BB was incubated on sections for one hour at room temperature. Control sections were incubated in PBS-BB alone. Sections were then washed in PBS (three X for five minutes each wash) and reacted for ten minutes at room temperature in a solution containing 4-(4-hydroxystyryl) pyridinium propylsulfonate (HPPS) (Molecular Biosciences; Boulder, Colo.) at 100 µg/ml in TSA Amplification Diluent, (NEN Life Science Products, Inc.; Boston, Mass.). Sections were then washed in PBS (three X for five minutes each wash), mounted in PBS:Glycerol (1:1) and coverslipped. Sections were viewed with a Zeiss Axioskop microscope equipped with epifluorescence and a filter set with excitation/emission characteristics of 360 nm peak excitation/>400 nm long pass emission. Photomicrographs were taken using a Zeiss MC100 camera system.

Figure 1B:
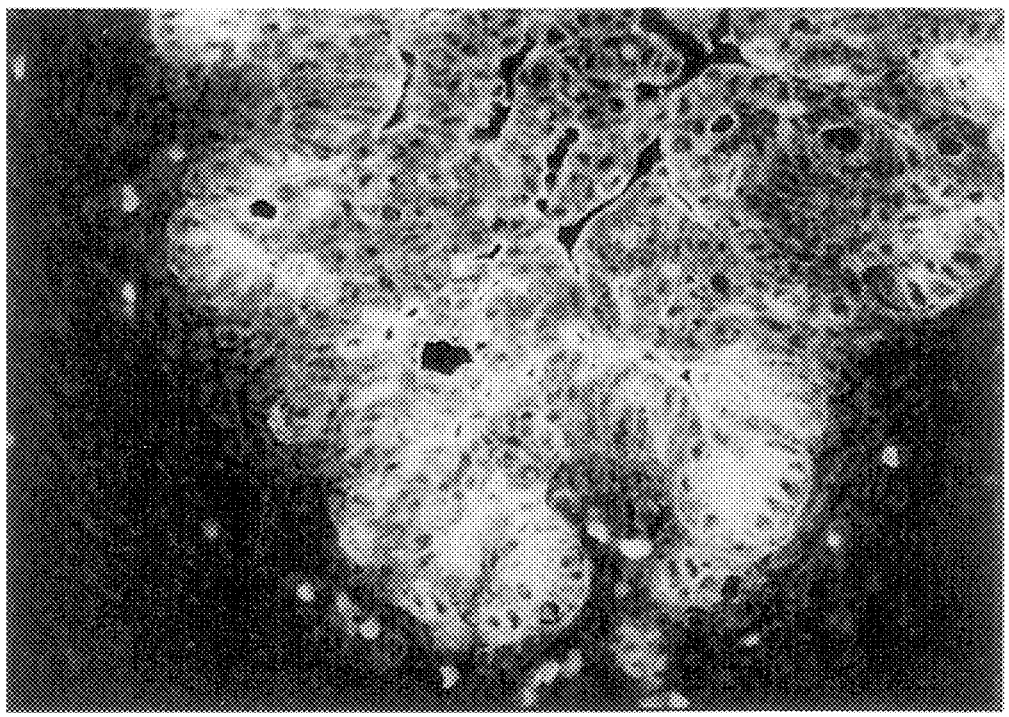
FIG. 1B is a photomicrograph illustrating a section of mouse intestine exposed to HRP-conjugated wheat germ agglutinin, the photomicrograph illustrating intense EPPS fluorescence localized to intestinal goblet cells.

No specific labeling was observed in sections incubated in PBS-BB without wheat germ agglutinin (FIG. 1A). In sections exposed to HRP-conjugated wheat germ agglutinin (FIG. 1B), intense HPPS fluorescence was localized to intestinal goblet cells which possess numerous wheat germ agglutinin binding sites. The concentration of HBP conjugated wheat germ agglutinin used here for HPPS detection (0.5 µg/ml) was significantly less than that required for wheat germ agglutinin localization using fluorescein conjugated wheat germ agglutinin (10 µg/ml). Original magnifications 400X.

EXAMPLE 2

Deposited 4-(4-hydroxystyryl) pyridine fluorescent reaction product is stable in non-aqueous medium.

Sections of paraffin-embedded mouse intestine were deparaffinized and non-specific binding sites were blocked by treatment for thirty minutes in PBS-BB. HRP conjugated wheat germ agglutinin (Sigma), at a concentration of 0.5 µg/ml in PBS-BB, was incubated on sections for one hour at room temperature. Sections were then washed in PBS (three X for five minutes each wash) and were reacted for ten minutes at room temperature in a solution of 4-(4-hydroxystyryl) methylpyridinium tosylate (HMPT) (Molecular Biosciences) at 100 µg/ml in TSA Amplification Diluent (NEN Life Science Products, Inc.). Sections were then washed in PBS (three X for five minutes each wash) and either mounted in PBS:Glycerol (1:1) or dehydrated in graded ethanol solutions (0%, 70%, 95%, 100%, 100% three minutes each) and xylene (two X for three minutes each) mounted in Permount (a non-aqueous mounting medium; Fisher Scientific, Pittsburgh, Pa.) and coverslipped. The fluorescent signal intensity of slides mounted in aqueous (PBS:Glycerol) or non-aqueous (Permount) media was compared using a Zeiss Axioskop microscope equipped with epifluorescence and a 360 nm excitation/>400 nm emission filter set. Photomicrographs were taken using a Zeiss MC100 camera system and standard two second exposures.

Figure 2A:
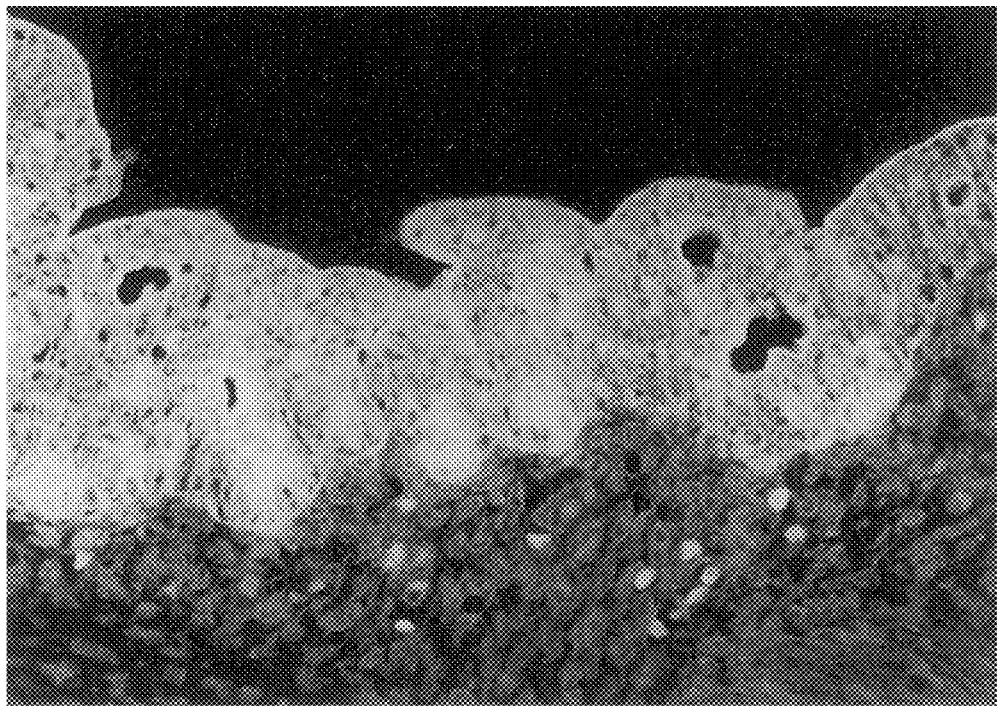
FIG. 2A is a photomicrograph illustrating a section of mouse intestine treated with HMPT, which exhibits a bright fluorescence in aqueous solution.
Figure 2B:
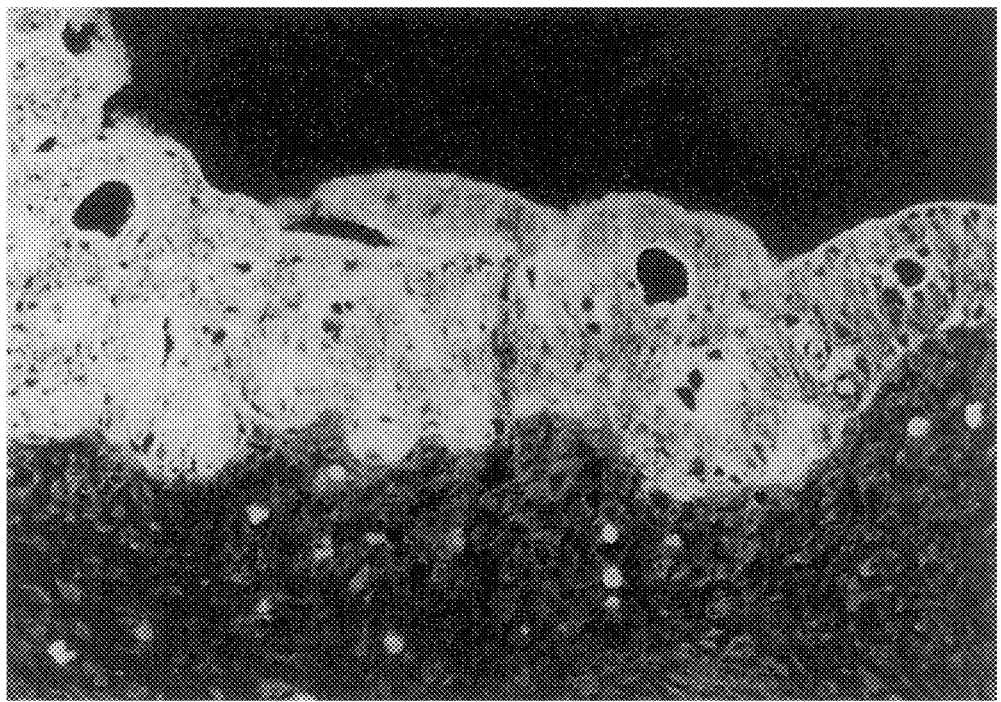
FIG. 2B is a photomicrograph illustrating a section of mouse intestine treated with HMPT, to produce a bright reaction product in a non-aqueous medium.

Unlike most conventional fluorophores which show significantly reduced fluorescence intensity in non-aqueous medium, HMPT reaction product was equally bright in aqueous (FIG. 2A) and non-aqueous (FIG. 2B) medium. In addition, when mounted in non-aqueous media, the background signal is reduced resulting in a better signal/noise ratio. Strong wheat germ agglutinin reactivity was localized to the intestinal epithelium under both conditions. Original magnifications 400X.

It should be clear to those skilled in the art that a large number of variations are possible and all these variations fall within the scope of the invention.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

What is claimed is:

1. A 4-(4-hydroxystyryl) pyridine-containing compound having the structure:

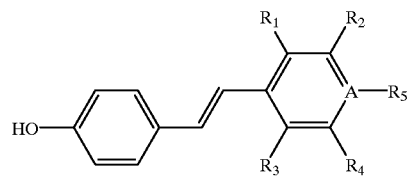

wherein $R_1$, $R_2$, $R_3$, and $R_4$ are independently H or —X—L, $R_5$ is an electron pair or —X—L, X is a linker group capable of linking L to a 4-(4-hydroxystyryl) pyridine moiety, L is a detectable label, A is N or $N^+$, and wherein when $R_1$, $R_2$, $R_3$, and $R_4$ are each H, $R_5$ is —X—L and A is $N^+$ and wherein when any of $R_1$–$R_4$ is —X—L, A is N and $R_5$ is an electron pair.

2. A compound according to claim 1, wherein L is a first member of a specific binding pair.

3. A compound according to claim 2, wherein L is biotin or dinitrophenyl.

4. A compound according to claim 1, wherein L is a fluorescent compound.

5. A compound according to claim 4, wherein L is fluorescein or tetramethylrhodamine.

6. A compound according to claim 1, wherein X includes a segment comprising $C_NH_{2N}$ wherein N is 1–10.

7. A compound according to claim 1, wherein X is —(CH$_2$)$_5$CONH(CH$_2$)$_5$NH—.

8. In an assay for detecting or quantitating an analyse, assay employing an analyte dependent enzyme activation system which reacts with a substrate portion of a conjugate which comprises a detectably labelled substrate for said enzyme, so as to form an activated conjugate, which activated conjugate covalently binds to a site on a surface having a receptor for said activated conjugate, said receptor not being reactive with the analyte dependent enzyme activation system, wherein the detectably labelled portion of the bound conjugate either directly or indirectly generates a signal which is detected or quantitated, the improvement comprising:

using as said conjugate the detectably labelled 4-(4-hydroxystyryl) pyridine containing compound of claim 1.

9. The assay according to claim 8, wherein the 4-(4-hydroxystyryl) pyridine-containing compound has the formula

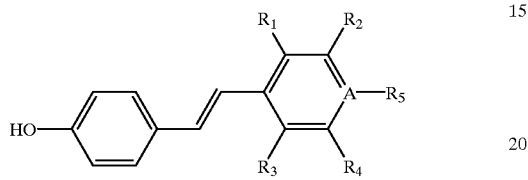

wherein $R_1$, $R_2$, $R_3$, and $R_4$ are independently H or —X—L, $R_5$ is an electron pair or —X—L, X is a linker group capable of linking L to a 4-(4-hydroxystyryl) pyridine moiety, L is a detectable label, A is N or $N^+$, and wherein when $R_1$, $R_2$, $R_3$, and $R_4$ are each H, $R_5$ is —X—L and A is $N^+$ and wherein when any of $R_1$–$R_4$ is —X—L, A is N and $R_5$ is an electron pair.

10. The assay according to claim 9, wherein X is —$(CH_2)_5CONH(CH_2)_5NH$—.

11. The assay according to claim 9, wherein L is selected from the group consisting of biotin, dinitrophenyl, fluorescein, and tetramethylrhodamine.

12. The assay according to claim 11, wherein the 4-(4-hydroxystyryl) pyridine-containing compound is

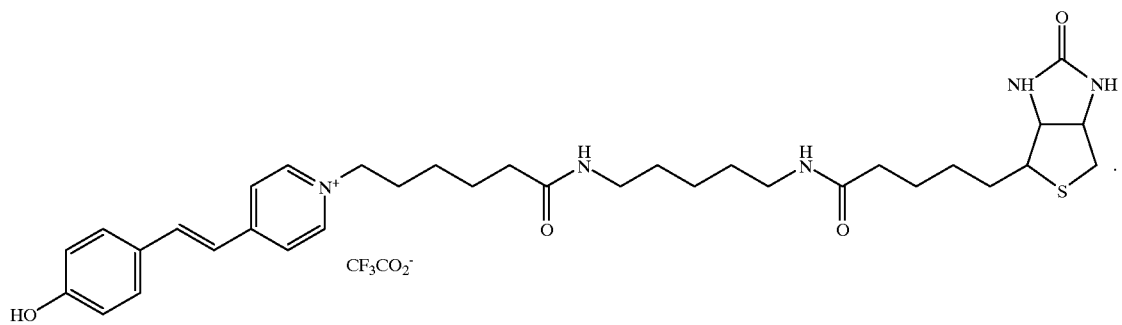

13. The assay according to claim 8, wherein the 4-(4-hydroxystyryl) pyridine-containing substrate has the formula:

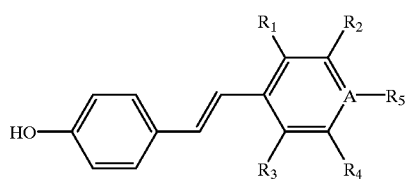

wherein $R_1$, $R_2$, $R_3$, and $R_4$ are H or Z; $R_5$ is an electron pair or Z, Z is a linear alkyl, a branched alkyl, a substituted alkyl, heteroalkyl or substituted heteroalkyl wherein the heteroatom is selected from the group consisting of N, O, or S; A is N or $N^+$ and wherein when $R_1$, $R_2$, $R_3$, and $R_4$ are H, $R_5$ is Z and A is $N^+$ and wherein when any of $R_1$–$R_4$ is Z, A is N.

14. The assay according to claim 13, wherein the 4-(4-hydroxystyryl) pyridine-containing compound is selected from the group consisting of

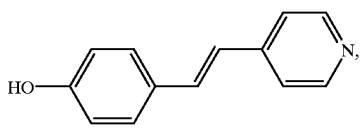

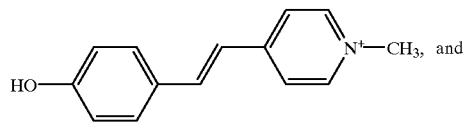

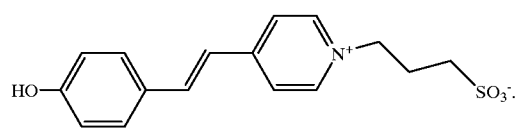

15. The assay according to claim 13, wherein the heteroalkyl includes a double bond.

16. The assay according to claim 13, wherein the heteroalkyl is substituted with a group selected from the group consisting of —OH, —COOH, —$NH_2$, and —SH.

17. The assay according to claim 8, wherein the enzyme is a peroxidase.

* * * * *